United States Patent
Geiger et al.

(10) Patent No.: US 10,272,188 B1
(45) Date of Patent: Apr. 30, 2019

(54) CEREBROSPINAL FLUID TREATMENT

(71) Applicant: Mensana Therapeutics LLC, Laguna Niguel, CA (US)

(72) Inventors: Mark Geiger, Laguna Niguel, CA (US); Michael V. Ward, San Ramon, CA (US)

(73) Assignee: Mensanan Therapeutics LLC, Laguna Nigel, CA (US)

( * ) Notice: Subject to any disclaimer, the term of this patent is extended or adjusted under 35 U.S.C. 154(b) by 264 days.

(21) Appl. No.: 14/803,589

(22) Filed: Jul. 20, 2015

Related U.S. Application Data

(60) Provisional application No. 62/027,892, filed on Jul. 23, 2014.

(51) Int. Cl.
  *A61M 1/16* (2006.01)
(52) U.S. Cl.
  CPC ... *A61M 1/1621* (2014.02); *A61M 2202/0464* (2013.01); *A61M 2205/10* (2013.01)
(58) Field of Classification Search
  CPC ........ A61M 27/006; A61M 2202/0464; A61M 1/1627; A61M 1/1621; A61M 1/1625; A61M 2205/10; A61N 1/36082; A16M 1/1627
  See application file for complete search history.

(56) References Cited

U.S. PATENT DOCUMENTS

| | | | |
|---|---|---|---|
| 4,446,155 A | 5/1984 | Osterholm | |
| 4,904,237 A | 2/1990 | Janese | |
| 4,995,401 A | 2/1991 | Bunegin et al. | |
| 5,385,541 A | 1/1995 | Kirsch et al. | |
| 5,772,625 A | 6/1998 | Krueger et al. | |
| 6,689,085 B1* | 2/2004 | Rubenstein | A61M 27/006 604/8 |
| 7,311,690 B2* | 12/2007 | Burnett | A61M 5/14276 604/9 |
| 7,887,503 B2 | 2/2011 | Geiger | |
| 8,435,204 B2* | 5/2013 | Lad | A61M 27/006 604/8 |
| 2006/0020239 A1 | 1/2006 | Geiger et al. | |
| 2008/0114337 A1 | 5/2008 | Ahmed | |
| 2009/0131850 A1* | 5/2009 | Geiger | A61M 27/006 604/9 |

(Continued)

OTHER PUBLICATIONS

Epstein et al., "Cerebrospinal Fluid Production: Stimulation by Cholera Toxin", Science Magazine, vol. 196, Issue 4293, pp. 1012-1013, May 27, 1977.

*Primary Examiner* — Brandy S Lee
(74) *Attorney, Agent, or Firm* — Moser Taboada

(57) ABSTRACT

Provided, among other things, is a method of treating cerebral spinal fluid comprising: (a) utilizing a channel of a pump to draw CSF from a subject's subarachnoid space of the subject's brain or spinal column; (b) subjecting the drawn CSF to membrane dialysis against a dialysate fluid to reduce immune or inflammatory mediators; and (c) utilizing a second channel of the synchronized dual channel pump to return the dialyzed CSF to the subarachnoid space of the subject's brain or spinal column. For example, the pump can be a synchronized dual channel pump. In one embodiment, the method further comprises: (d) removing cellular matter from the CSF to produce reduced cell content CSF, wherein the reduced cell content CSF is subjected to membrane dialysis.

13 Claims, 4 Drawing Sheets

(56) References Cited

U.S. PATENT DOCUMENTS

2010/0305492 A1* 12/2010 Lad .................... A61M 27/006
604/9
2015/0094644 A1 4/2015 Lenihan et al.

* cited by examiner

CEREBROSPINAL FLUID TREATMENT

CROSS-REFERENCE TO RELATED APPLICATION

This application claims benefit of U.S. Provisional Patent Application No. 62/027,892 filed Jul. 23, 2014, which is incorporated herein by reference in its entirety.

Defined herein is a unique medical device therapy for neuroinflammatory diseases and disorders, which are manifested and exacerbated by inflammatory mediators, which can be proteins and/or cells.

Cerebrospinal fluid ("CSF") is made by cells of the choroid plexus found in a number of parts of the ventricular system. As it flows through the ventricular system it is distributed into cisterns of the subarachnoid space and into the central canal of the spinal cord. In healthy circumstances, CSF is constantly re-absorbed, turning over several times a day.

Filtering CSF has been proposed as a method of conditioning CSF to ameliorate disease states. Wollinsky treated patients with Guillain Barre Syndrome, an immune-mediated neurological disease, using an extracorporeal makeshift device that included a commercial filter that removed proteins from the draining CSF. Patients experienced improvements in clinical signs and symptoms.[11 & 12]

What has not been suggested is membrane dialysis to reduce the number of lower molecular weight immune mediators.

SUMMARY

Provided, in one embodiment, is a method of treating cerebral spinal fluid comprising: (a) utilizing a channel of a pump to draw CSF from a subject's subarachnoid space of the subject's brain or spinal column; (b) subjecting the drawn CSF to membrane dialysis against a dialysate fluid to reduce immune or inflammatory mediators; and (c) utilizing a second channel of the synchronized dual channel pump to return the dialyzed CSF to the subarachnoid space of the subject's brain or spinal column. For example, the pump can be a synchronized dual channel pump. In one embodiment, the method further comprises: (d) removing cellular matter from the CSF to produce reduced cell content CSF, wherein the reduced cell content CSF is subjected to membrane dialysis.

The method, in embodiments, reduces cellular material by: flow centrifugation effective to reduce cell content; subjecting a flow pathway for the CSF to magnetic or electrical fields that cause cells to bias towards flowing through one or more side channels; flowing the CSF through a filter with pores sized to retain human or other vertebrate cells; flowing the CSF through a charged filter effective to retain human or other vertebrate cells; or flowing the CSF through a first charged filter effective to retain human or other vertebrate cells and an oppositely charged filter effective to retain human or other vertebrate cells.

In embodiments, the invention provides a method of treating or ameliorating brain disease such as cerebral hemorrhage comprising applying the above method to the subject. The method can be treating or ameliorating acute brain injury, or treating or ameliorating encephalitis, or treating or ameliorating meningitis, or treating or ameliorating Alzheimer's disease, or treating or ameliorating Parkinson's disease.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1:
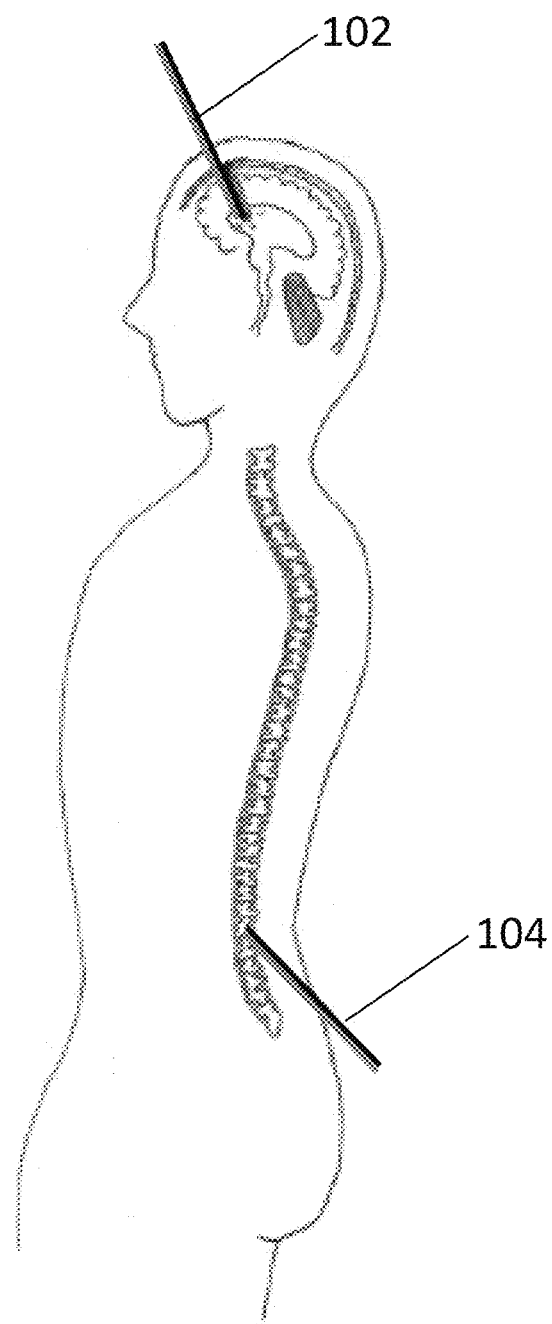
FIG. 1 schematically depicts a human with two catheters inserted into the cerebral (102) and lumbar (104) subarachnoid space.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Many central nervous system diseases and disorders begin and often continue with a neuroinflammatory pathway to the point of being pathological. These pathways involve one or more of antibodies/immune complexes, immune cells, and a variety of inflammatory mediators, which include the complement system and cytokines (soluble proteins, peptides, or glycoproteins). Examples of cytokines include interleukins and interferons.[1, 3, 4, 5, 6, 7, 9, 10]

When there is an initial insult to the body, whether slow-progressing chronic disease or sudden acute phase medical insult (trauma or infection, for example), cytokines are an important component of the initial inflammatory response necessary to recruit granulocytes and, later on, lymphocytes, to fight the elements of the initial insult. As this part of an acute phase inflammatory response continues, these same cytokines may do more harm than good and exacerbate pathologic processes.[2]

Self-sustaining inflammatory pathways involving complement, interleukins, and a myriad of neuroinflammatory mediators have been evidenced in acute inflammatory disorders and in chronic brain diseases such as Parkinson's disease and Alzheimer's disease.[1, 6, 7]

Though a different anatomical location, outside the brain, a description of pancreatitis[2] clearly models identical pathways associated with neuroinflammatory processes.

Without being bound by theory, it is believed that reducing the level of these pro-inflammatory components with the methods of the invention contribute to treating a number of indications.

CSF is a clear colorless body fluid, produced in the choroid plexus of the brain. It acts as a cushion or buffer for the cerebral cortex, providing a basic mechanical and immunological protection to the brain inside the skull and serves a vital function in cerebral autoregulation of cerebral blood flow.

The CSF occupies the subarachnoid space (the space between the arachnoid mater and the pia mater) and the ventricular system around and inside the brain and spinal cord. It constitutes the content of the ventricles, cisterns, and sulci of the brain, as well as the central canal of the spinal cord, and is in adult humans approximately 150 ml in volume.

CSF is produced in the brain by modified ependymal cells in the choroid plexus (approx. 50-70%) and the remainder is formed around blood vessels and along ventricular walls. It circulates from the lateral ventricles through the foramina of Monro (Interventricular foramina), third ventricle, aqueduct of Sylvius (Cerebral aqueduct), fourth ventricle, foramen of Magendie (Median aperture) and foramina of Luschka (Lateral apertures), subarachnoid space over brain and spinal cord. It should be noted that the CSF moves in a pulsatile manner throughout the CSF system with nearly zero net flow. CSF is reabsorbed into venous sinus blood via arachnoid granulations.

CSF is produced at a rate generally of at least of 500 ml/day. Since the subarachnoid space around the brain and spinal cord can contain only 135 to 150 ml, large amounts are drained primarily into the blood through arachnoid granulations in the superior sagittal sinus. The production rate is thought to be approximately 500 ml/day; thus, the CSF turnover rate is about 3.7 times a day.

CSF is a weak salt solution with similar inorganic ion concentrations to plasma, but with small and significant differences. The protein content is about 100 times less than that of plasma, containing approximately 0.3% of the protein concentration found in normal plasma. Under non-pathological conditions the time for diffusion of serum albumin protein from plasma into CSF is about one day; whereas, for IgM, diffusion time is several days. The diffusion controlled transfer of proteins from serum into CSF represents the actual blood-CSF barrier function. A summary of CSF content is found in Table 1.

TABLE

| Composition of Normal CSF | |
|---|---|
| Component | Concentration |
| Protein | 15-40 mg/dL |
| Albumin | 7.8-40 mg/dL |
| IgG | 2.7-6.5 mg/dL |
| RBCs | 0 |
| WBCs | 0-3 cells/µL |
| pH | 7.28-7.32 |

Described herein is a means of treating many neuroinflammatory disorders, some of which have been noted above; but, the list is not exclusive as pathogeneses of various neurological disorders often change with the advent of new published research. For instance, Alzheimer's disease was thought, until very recently, to be exclusively caused by beta amyloid and pharmaceutical companies and academic scientific laboratories focused upon disrupting the production and/or excretion pathways of beta amyloid. More recent studies have suggested that beta amyloid may be secondary to other pathological processes involving cytokines.[13, 14 & 15]

As shown in FIG. 1, catheters can be used to access the subarachnoid space, such as a lateral ventricle, or the spinal column. In embodiments, a single, multi-lumen catheter is used. For example, standard catheters as used for ventricular-peritoneal shunts can be used.

Figure 2:
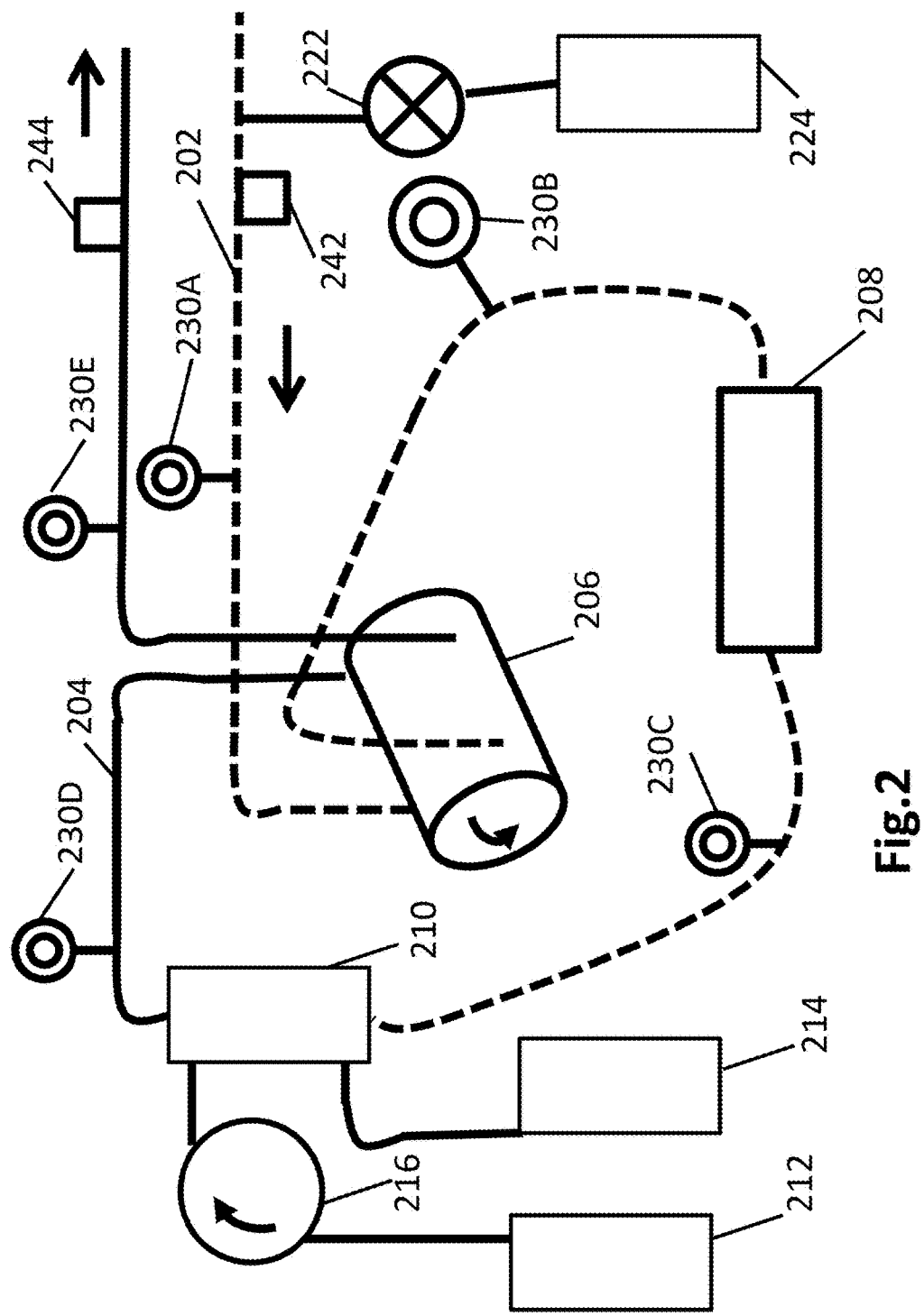
FIG. 2 is a schematic diagram of an apparatus for conducting an embodiment of the invention.
Figure 3:
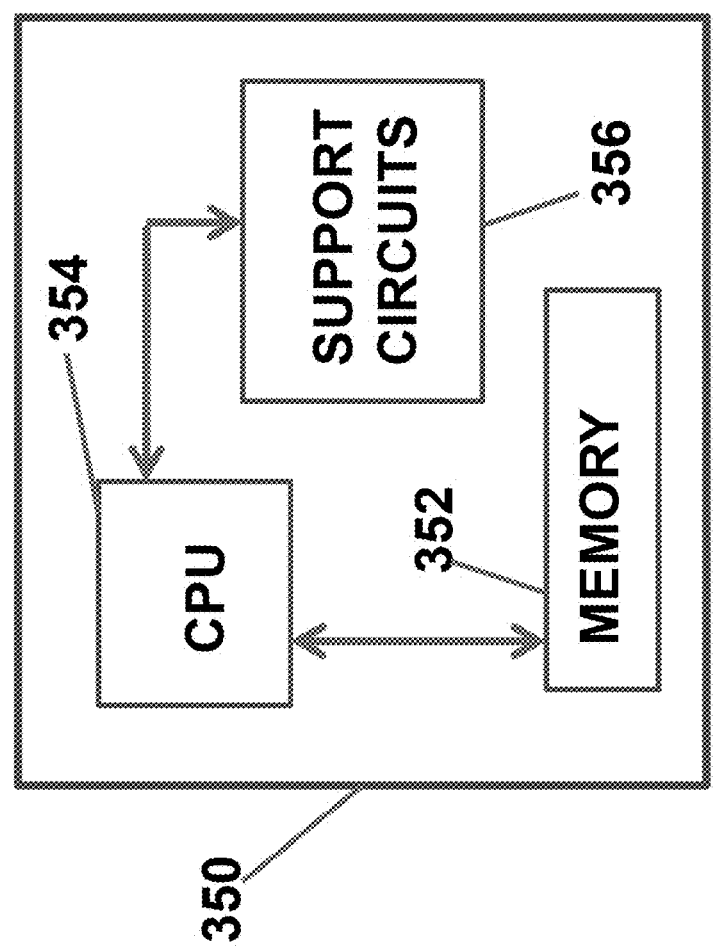
FIG. 3 is a controller that can be used to operate the apparatus.

As illustrated in FIG. 2, an outward fluid line 202 draws CSF from a subject (e.g., animal, such as human) via a pump 206, which can be a synchronized dual channel pump. A synchronized dual channel pump is a pump or coordinated combination of pumps where the pumping applied to one line is coordinated with the pumping in a second line in a fixed ratio of flow, such as 1:1. An example of a synchronized dual channel pump is a roller pump. Automated valving between redundant channels with different tubing sizes can be used to adjust the relative flow rates of the two lines.

In embodiments, the fluid is drawn through a cell separator 208 (device for removing cellular material). This is illustrated as occurring after the CSF passes through pump 206, but this ordering is optional.

The flow rates into and out of the subarachnoid space will generally be equal to assure that ventricular volumes and pressures are minimally altered. The pump will be connected to pressure sensors that will contribute to the balancing of outflow and inflow of CSF. One exception to this balancing of flows can be when there is an excess of fluid in the brain from such circumstances as acute brain injury. In these instances, outflow rates might exceed inflow rates to achieve a normalized CSF volume and pressure within the brain.

In normal CSF, the cell concentrations are much lower than in blood. In fact red blood cells are not present in normal CSF. However, in certain neurological conditions, such as infections or brain trauma, the cellular levels in CSF will be much higher, possibly including the presence of red blood cells.

The fluid is drawn through dialyzer 210, and returned to the subarachnoid space via outward fluid line 204. Dialyzer 210 operates with a dialysate fluid such as provided from dialysate input reservoir 212. If the treatment requires changing out the dialysate fluid during the process, dialysate output reservoir 214 can be used. Dialysate can be inputed into the dialyzer 210 by, for example, pump 216.

The internal core to dialyzer 201 can be a standard fiber structure used in hemodialysis, including but not limited to liquid purification ultrafilters, microfibers, and/or nanofibers.

One or more of sensors 230 can be used to monitor the treatment process, such as via pressure sensing. A pressure sensor can be inserted with, or integral with, the catheter, or otherwise provided in the subarachnoid space. Sensors 230A and 230E can include flow rate sensors, such that the controller can operate to assure appropriate flow back into the subarachnoid space to equalize the effect of withdrawal.

If the fluid at sensor 230A or the subarachnoid sensor indicates elevated pressure, the process of the invention may be operated to return less fluid than it draws. This can be done by controlling the flow at the inward and outward fluid lines via pump 206, or by operating valve 222 to draw a portion of the fluid off, for example to CSF reservoir 224.

Similar flow rate controls can be done if the dialyzer is operated to provide a net decrease in CSF volume or a net increase. While not shown, a second operating valve can be operated to shunt CSF away from return to the subarachnoid space as needed. Flow sensors for the incoming and outgoing fluid from the dialyzer can be used, or pressure monitoring, including dialysate pressure monitoring, can be used to determine if a net increase or decrease in volume occurs at the dialyzer.

In embodiments, sampling port 242 allows measurements of cell counts, protein concentrations, and the like. In embodiments, sampling port 244 allows measurements of cell counts, protein concentrations, and the like, as well as administration of drugs to the ventricular space, thus bypassing the blood-brain barrier and theoretically allowing much lower doses that might be administered by other routes (parenteral, oral etc.).

One example of a cell separator is a continuous flow centrifugation device whereby the denser material of cells is sedimented to reduce the concentration that flows through cell separator 208. The g-force needed to reduce cell concentration is generally much less than the capability of such devices. A concentrated flow of cellular material can continuously flow into a cellular material reservoir (e.g., collection bag, not shown).

Figure 4:
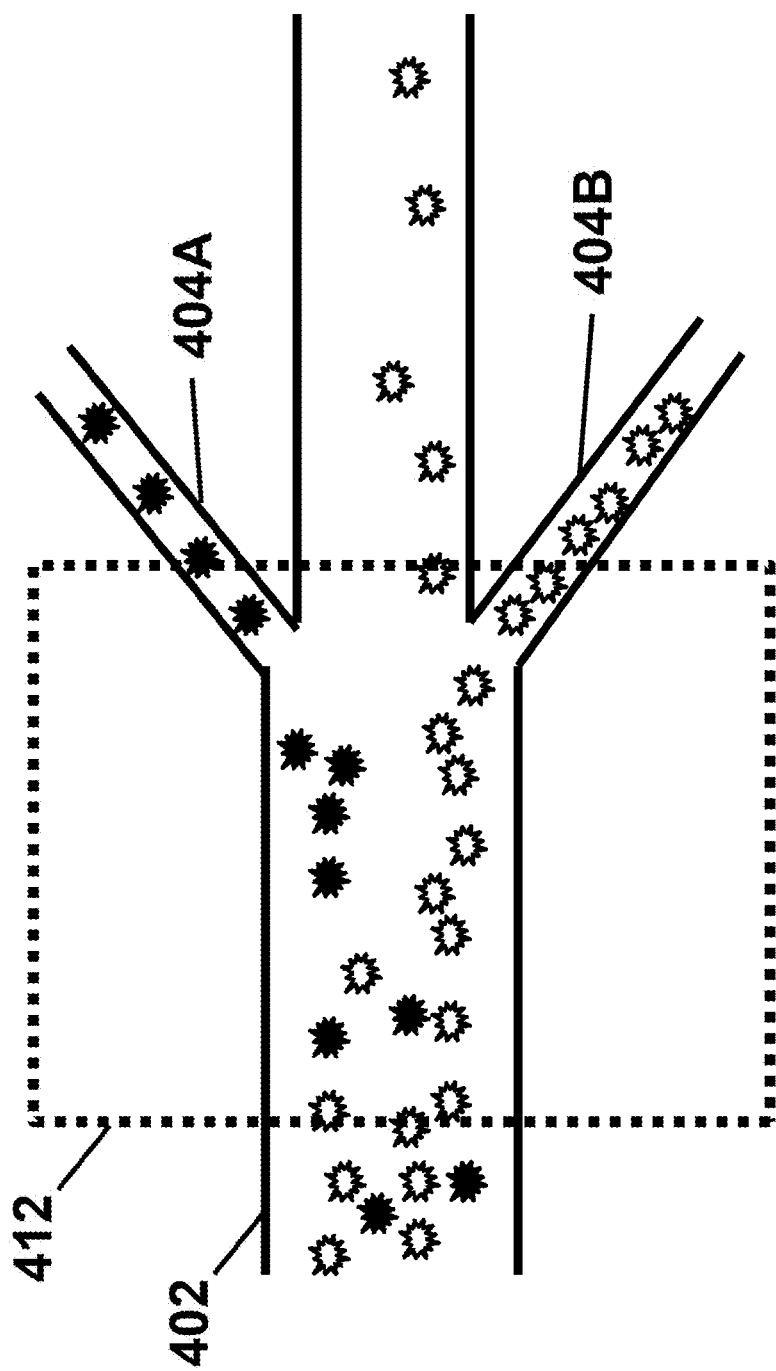
FIG. 4 is a schematic of one of several types of field/force-induced cell separators.

Another example of a cell separator is one that subjects a flow pathway for the CSF to magnetic or electrical fields that cause cells to bias towards flowing through one or more side channels (e.g. for separate collection). Separate zones can be adapted to bias certain cells out of the primary flow pathway. See, Micromachines 2011, 2, 319-343; doi:10.3390/mi2030319, which is incorporated herein in its entirety concerning cell separation techniques and devices (which can be used as the cell separator 208). In FIG. 4, field-producer 412 biases certain cells in channel 402 to side channel 404A, and others to side channel 404B.

Another example of a cell separator is one that subjects a flow pathway for the CSF to flow through a filter with pores sized to retain human and other vertebrate animal blood and inflammatory cells. The pore size does not need to be small enough to trap bacteria but should be of a size capable of removing all vertebrate cells: platelets are about 2-3 micrometer in diameter; white blood cells and erythrocytes are ≥6 micrometer in diameter. Staging of pore sizes can be used to increase the life-span of the filtering device.

Another example of a cell separator is one that subjects a flow pathway for the CSF to flow through a charged filter effective to retain human and other vertebrate cells. Filters in these embodiments can have pores larger than would be used without the charge feature. Such filters are available for example from Pall Corporation, East Hills, N.Y. Staging of pore sizes, including uncharged preliminary filters, can be used to increase the life-span of the charged filtering device.

Another example of a cell separator is one that directs the CSF flow through a first charged filter effective to retain some cell types and an oppositely charged filter effective to retain other cell types. Filters in these embodiments in embodiments can have pores larger than would be used without the charge feature. Such filters are available for example from Pall Corporation, East Hills, N.Y. Staging of pore sizes, including uncharged preliminary filters, can be used to increase the life-span of the charged filtering device.

The membrane pore size used in the dialyzer 210 can be for example one that retains proteins of 10,000 Daltons or more, or 6,000 Daltons or more, or 5,000 Daltons or more, or 3,000 Daltons or more.

While not being bound by theory, it is believed that a number of harmful inflammatory mediators (proteins) have much larger molecular weights than what is quoted above Examples include certain leukotrienes, histamine, proteases, and heparin. While not being bound by theory, a corollary removal of immune response cells can further enhance treatment effectiveness.

The controller 350 comprises a central processing unit (CPU) 354, a memory 352, and support circuits 356 for the CPU 354 and is coupled to and controls one or more of the various elements of the CSF treatment device or, alternatively, via computers (or controllers) associated with CSF treatment device. The controller 350 may be one of any form of general-purpose computer processor that can be used for controlling various devices and sub-processors, or a network of computing devices. The memory, or computer-readable medium, 352 of the CPU 354 may be one or more of readily available memory such as random access memory (RAM), read only memory (ROM), flash memory, floppy disk, hard disk, or any other form of digital storage, local or remote. The support circuits 356 are coupled to the CPU 354 for supporting the processor in a conventional manner. These circuits can include cache, power supplies, clock circuits, input/output circuitry and subsystems, and the like. Methods of operating the CSF treatment device may be stored in the memory 352 as software routine that may be executed or invoked to control the operation of the CSF treatment device, such as monitoring pressure from a sensor 230, adjusting the pump rate of one or more channels in pump 206, adjusting dialysate flow rate, and the like. The software routine may also be stored and/or executed by a second CPU (not shown) that is remotely located from the hardware being controlled by the CPU 354.

It will be recognized by clinicians "treating" includes reducing, alleviating, ameliorating, eliminating or preventing one or more symptoms of the condition sought to be treated, or alternately, the condition sought to be avoided, or to otherwise produce a clinically recognizable favorable change in the condition or its effects.

Specific embodiments according to the methods of the present invention will now be described in the following examples. The examples are illustrative only, and are not intended to limit the remainder of the disclosure in any way.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

REFERENCES

1. Swardfager W, Lanctôt K, Rothenburg L, Wong A, Cappell J, and Herrmann N. A meta-analysis of cytokines in Alzheimer's disease. Biol. Psychiatry (November 2010), Vol 68 (10): 930-41.
2. Makhija R and Kingsnorth A N. Cytokine storm in acute pancreatitis. J Hepatobiliary Pancreat Surg (2002), Vol 9 (4): 401-1.
3. Le Maitre E, Lundberg K, Kosek E, Khademi M, Andersson M, and Lampa J. Unexpected finding of anti-citrullinated protein antibodies (ACPA) in cerebrospinal fluid of RA patients with intact blood brain barrier-potential for autoimmune reactions in the CNS. Annals of the Rheumatic Disease (2013), Vol 71, SUPPL. 3.
4. Szmydynger-Chodobska J, Gandy J R, Varone A, Shan R, and Chodobski A. Synergistic Interactions between Cytokines and AVP at the Blood-CSFBarrier Result in Increased Chemokine Production and Augmented Influx of Leukocytes after Brain Injury. PLoS ONE (2013), Vol 8(11): e79328.
5. Bijay P, Yoshifumi S, Jun K, Yukiko D, Mariko N, Hideyuki T,
Tetsuya M, and Akio S. G M-CSF increases LPS-induced production of pro-inflammatory mediators via up regulation of TLR4 and CD14 in murine microglia. Journal of Neuroinflammation (2012), Vol 9: 268.

6. Jo Yuan Sun, Xue Song Yin, Hong Guo, Rong Kun Han, Rui Dong He, and Li Jun Chi. Elevated Osteopontin Levels in Mild Cognitive Impairment and Alzheimer's Disease. Mediators of Inflammation (Hindawi Publishing Corporation), Volume 2013, Article ID 615745.
7. Michigan State University. Brain Inflammation Linked to More Severe Parkinson's Symptoms. Medical Design Technology (Aug. 29, 2013).
8. Tunkel A R, Glaser C A, Bloch K C, Sejvar J J, Marra C M, Roos K L, Hartman B J, Kaplan S L, Scheld W M, and Whitley R J. The Management of Encephalitis: Clinical Practice Guidelines by the Infectious Diseases Society of America. Clinical Infectious Diseases (2008), Vol 47: 303-327.
9. Griffin D E. Immunoglobulins in the cerebrospinal fluid: changes during acute viral encephalitis in mice. Journal of Immunology (January 1981), Vol 126 (1): 27-31.
10. Griffin D E and Giffels J. Study of Protein Characteristics That Influence Entry into the Cerebrospinal Fluid of Normal Mice and Mice with Encephalitis. Journal of Clinical Investigation (August 1982) Vol 70: 289-295.
11. Wollinsky K H, Hulser P J, Westarp M E, Mehrkens H H, and Kornhuber H H. Cerebrospinal Fluid Pheresis in Guillain Barre Syndrome. Medical Hypothesis (1992), Vol 38: 155-165.
12. Wollinsky K H, Hulser P J, Brinkmeier H, et al. CSF filtration is an effective treatment of Guillain-Barre syndrome: A randomized clinical trial. Neurology (2001), Vol 57: 774-780.
13. Sue T & Griffin T. Neuroinflammatory Cytokine Signaling and Alzheimer's disease. NEJM (Feb. 21, 2013) Vol 368 (8): 770-771.
14. Zetterberg H, David Wilson, et al Plasma tau levels in Alzheimer's disease. Alzheimer's Research & Therapy (2013), Vol 5: 9.
15. Marques 0 & Outeiro T F. Alpha-synuclein: from secretion to dysfunction and death. Cell Death and Disease (2012) Vol 3: e350.
16. Chu J. Microchip Sorts White Blood Cells from Whole Blood. Medical Design Technology (Aug. 6, 2013).
17. How H W, Gan H Y, Bhagat A A S, Li L D, and Lim C T. A microfluidics approach towards high-throughput pathogen removal from blood using margination. Biomicrofluidics (2012), Vol 6: 024115.
18. Seo, J., Lean, M. H. & Kole, A. Membrane-free microfiltration by asymmetric inertial migration. Appl. Phys. Letter (2007) Vol 91: 3.
19. Di Carlo, D., Irimia, D., Tompkins, R. G. & Toner, M. Continuous inertial focusing, ordering, and separation of particles in microchannels. Proc. Natl. Acad. Sci. U.S.A (2007)104, 18892-18897.
20. Di Carlo, D. Inertial microfluidics. Lab Chip (2009) 9, 3038-3046.
21. Bhagat, A. A. S., Hou, H. W., Li, L. D., Han, J. Y.& Lim, C. T. Pinched flow coupled shear-modulated inertial microfluidics for high-throughput rare blood cell separation. (2011) Lab Chip 11, 1870-1878.

The invention includes the following numbered embodiments:

Embodiment 1

A method of treating cerebral spinal fluid comprising: (a) utilizing a channel of a pump to draw CSF from a subject's subarachnoid space of the subject's brain or spinal column; (b) subjecting the drawn CSF to membrane dialysis against a dialysate fluid to reduce immune or inflammatory mediators; and (c) utilizing a second channel of the synchronized dual channel pump to return the dialyzed CSF to the subarachnoid space of the subject's brain or spinal column.

Embodiment 2

The method of embodiment 1, wherein the pump is a synchronized dual channel pump.

Embodiment 3

The method of embodiment 1, further comprising: (d) removing cellular matter from the CSF to produce reduced cell content CSF, wherein the reduced cell content CSF is subjected to membrane dialysis.

Embodiment 4

The method of embodiment 3, wherein the pump is a synchronized dual channel pump.

Embodiment 5

The method of embodiment 3 or 4, wherein the reducing cellular material comprises: flow centrifugation effective to reduce cell content; subjecting a flow pathway for the CSF to magnetic or electrical fields that cause cells to bias towards flowing through one or more side channels; flowing the CSF through a filter with pores sized to retain human or other vertebrate cells; flowing the CSF through a charged filter effective to retain human or other vertebrate cells; or flowing the CSF through a first charged filter effective to retain human or other vertebrate cells and an oppositely charged filter effective to retain human or other vertebrate cells.

Embodiment 6

A method of treating or ameliorating cerebral hemorrhage comprising applying the method of one of embodiments 1-5 to the subject.

Embodiment 7

A method of treating or ameliorating acute brain injury comprising applying the method of one of embodiments 1-5 to the subject.

Embodiment 8

A method of treating or ameliorating encephalitis comprising applying the method of one of embodiments 1-5 to the subject.

Embodiment 9

A method of treating or ameliorating meningitis comprising applying the method of one of embodiments 1-5 to the subject.

Embodiment 10

A method of treating or ameliorating Alzheimer's disease comprising applying the method of one of embodiments 1-5 to the subject.

Embodiment 11

A method of treating or ameliorating Parkinson's disease comprising applying the method of one of embodiments 1-5 to the subject.

This invention described herein is of a cerebrospinal fluid treatment. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A method of treating cerebral spinal fluid (CSF) comprising:
   utilizing a channel of a synchronized dual channel pump to draw out of the body CSF from a subject's subarachnoid space of the subject's brain or spinal column;
   removing cellular matter from the drawn, extracorporeal CSF to produce reduced cell content CSF;
   subjecting the drawn, filtered, extracorporeal CSF to membrane dialysis against a dialysate fluid to reduce immune or inflammatory mediators; and
   utilizing a second channel of the synchronized dual channel pump to return the dialyzed CSF to the subarachnoid space of the subject's brain or spinal column.

2. The method of claim 1, wherein the reducing cellular material comprises:
   flow centrifugation effective to reduce cell content;
   subjecting a flow pathway for the CSF to magnetic or electrical fields that cause cells to bias towards flowing through one or more side channels;
   flowing the CSF through a charged filter effective to retain human or other vertebrate cells; or
   flowing the CSF through a first charged filter effective to retain human or other vertebrate cells and an oppositely charged filter effective to retain human or other vertebrate cells.

3. A method of treating or ameliorating cerebral hemorrhage comprising applying the method of claim 1 to the subject.

4. A method of treating or ameliorating acute brain injury comprising applying the method of claim 1 to the subject.

5. A method of treating or ameliorating encephalitis comprising applying the method of claim 1 to the subject.

6. A method of treating or ameliorating meningitis comprising applying the method of claim 1 to the subject.

7. A method of treating or ameliorating Alzheimer's disease comprising applying the method of claim 1 to the subject.

8. A method of treating or ameliorating Parkinson's disease comprising applying the method of claim 1 to the subject.

9. The method of claim 1, wherein the reducing cellular material comprises flow centrifugation effective to reduce cell content.

10. The method of claim 1, wherein the reducing cellular material comprises subjecting a flow pathway for the CSF to magnetic or electrical fields that cause cells to bias towards flowing through one or more side channels.

11. The method of claim 1, wherein the reducing cellular material comprises flowing the CSF through a filter with pores sized to retain human or other vertebrate cells.

12. The method of claim 1, wherein the reducing cellular material comprises flowing the CSF through a charged filter effective to retain human or other vertebrate cells.

13. The method of claim 1, wherein the reducing cellular material comprises flowing the CSF through a first charged filter effective to retain human or other vertebrate cells and separately an oppositely charged filter effective to retain human or other vertebrate cells.

* * * * *